(12) United States Patent
Sardashti et al.

(10) Patent No.: US 7,982,872 B2
(45) Date of Patent: Jul. 19, 2011

(54) RESIDUAL CHEMICAL MONITORING SYSTEM USING SURFACE ENHANCED RAMAN SPECTROSCOPY

(75) Inventors: Maziar Sardashti, Bartlesville, OK (US); David J. Blumer, Bartlesville, OK (US); Frank J. McEnroe, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 12/861,584

(22) Filed: Aug. 23, 2010

(65) Prior Publication Data

US 2011/0043800 A1 Feb. 24, 2011

Related U.S. Application Data

(63) Continuation-in-part of application No. 12/116,415, filed on May 7, 2008, now Pat. No. 7,782,448, and a continuation-in-part of application No. 12/047,141, filed on Mar. 12, 2008, now Pat. No. 7,876,425.

(51) Int. Cl.
*G01J 3/44* (2006.01)
(52) U.S. Cl. ..................................................... 356/301
(58) Field of Classification Search .......... 356/300–340, 356/72–73
See application file for complete search history.

(56) References Cited

U.S. PATENT DOCUMENTS 5,112,127 A * 5/1992 Carrabba et al. .............. 356/301
* cited by examiner

*Primary Examiner* — Tarifur Chowdhury
*Assistant Examiner* — Abdullahi Nur

(57) ABSTRACT

Target chemicals are monitored at very low concentrations in pipelines or vessels such as storage tanks using surface enhanced Raman spectroscopy analysis of a sample. A liquid sample having a target chemical such as biocides, corrosion inhibitors, scale inhibitors, anti-foaming agents, emulsion breakers, and hydrate inhibitors are tested while exposed to a prepared and charged surface of a coupon so as to draw the target material to the prepared and charged surface. The charged surface is fairly precisely charged using two other electrodes to calibrate the charge on the surface of the coupon. With the target substance presumably drawn to the coupon, the molecules on the surface of the coupon are excited by monochromatic light such as from a laser to induce vibrations within the molecules. The vibrations of the molecules reflect and scatter the monochromatic light in distinctive manners such that the collected light from the surface provides an indication of the presence of the target substance in the sample and a quantitative indication of the concentration of the target material in the sample. With the ability at lower power and reasonable cost to sense the presence well down below one percent and into the ppm range provides the opportunity to more precisely and efficiently add such chemicals to operating pipelines and storage tanks.

13 Claims, 2 Drawing Sheets

RESIDUAL CHEMICAL MONITORING SYSTEM USING SURFACE ENHANCED RAMAN SPECTROSCOPY

CROSS-REFERENCE TO RELATED APPLICATIONS

This application is a continuation-in-part application which claims benefit under 35 USC §120 to U.S. application Ser. No. 12/047,141 filed Mar. 12, 2008, entitled "METHOD AND APPARATUS FOR SURFACE ENHANCED RAMAN SPECTROSCOPY," and a continuation-in-part application which claims the benefit under 35 USC §120 to U.S. application Ser. No. 12/116,415 filed May 7, 2008, entitled "METHOD AND APPARATUS FOR SURFACE ENHANCED RAMAN SPECTROSCOPY," issued Aug. 24, 2010 as U.S. Pat. No. 7,782,448, both of which are incorporated herein in their entirety. A related patent application is filed on the same date as this patent application entitled "On-Line/At-Line Monitoring of Residual Chemical by Surface Enhanced Raman Spectroscopy".

STATEMENT REGARDING FEDERALLY SPONSORED RESEARCH OR DEVELOPMENT

None.

FIELD OF THE INVENTION

This invention relates to monitoring the presence of chemicals in solutions in pipelines and to periodically testing the materials for the presence of certain chemicals.

BACKGROUND OF THE INVENTION

In the process of operating pipelines for transport, and vessels and tanks for storage of natural gas, petroleum and petroleum products, a large variety of chemicals may be used to protect the integrity of these vessels. These chemicals can act as biocides, corrosion inhibitors, scale inhibitors, anti-foaming agents, emulsion breakers, and hydrate inhibitors to name a few.

The chemicals are added in small, but effective amounts where effectiveness may in many cases be maintained below a one percent concentration. These chemicals tend to be expensive so small amounts are good for cost minimization and also avoid displacing the fluids such as oil, gas or fuels in the pipeline. However, small effective amounts are very slightly more than amounts that are inadequate and ineffective. These protective chemicals are typically consumed at non-linear and unpredictable rates so trying to maintain a minimum, but yet effective amount is very difficult. There are two fundamental challenges for efficient use of these types of chemicals. First, equipment that is reliable and cost effective for measuring chemical concentrations below one percent are generally unavailable or impractical. Secondly, since the chemical concentration may fall below the threshold for effective amounts without warning, it is common for pipeline operators and owners of vessels and storage tanks to simply use quite a bit more than necessary as a precaution against not having enough. Since the chemicals are very expensive, any over-use of the chemicals can directly and substantially impact the bottom line of the end-user. Therefore, it is highly desirable to have a mechanism to closely monitor the amounts of the chemicals to make sure that a minimum effective amount is present in the storage vessel or along the length of a pipeline at all times.

SUMMARY OF THE INVENTION

The invention more particularly relates to a system for determining the presence and concentration of a target substance within a liquid material in a pipeline or vessel that includes a chamber connected in fluid communication to the pipeline or vessel and arranged to receive and accumulate samples of a liquid material directly from the pipeline or vessel through an inlet and return samples back to the pipeline or vessel. A coupon having an electrically conductive surface is positioned within the chamber and an electrical charging system is arranged to provide an electric charge on the coupon. A counter electrode within the vessel and spaced from the coupon is arranged for sensing an electric charge on the coupon and through a sample liquid material within the vessel. A reference electrode is arranged within the chamber and spaced from each of the coupon and the counter electrode for sensing an electric charge on the electrode and through a sample liquid material within the chamber and also through a reference fluid that is physically isolated from any sample liquid material in the vessel but in electrochemical communication with any sample liquid within the vessel. An electrical charging system is arranged to provide the electric charge on the coupon and adjusting the precise electrical charge based on input from the counter electrode and reference electrode so as to provide a precise electric charge that draws molecules of the target substance to the surface of the coupon. An optical component with a light source is arranged for directing light to the electrically conductive surface of the coupon to induce vibrational responses of and within the molecules of the liquid material and a sensor for collecting and measuring light scattered by the vibrating molecules on the surface of the coupon. A spectrometer is arranged for interpreting the scattered light to provide information regarding the presence and quantificational information of the target substance within the liquid material in the pipeline or vessel.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

Turning now to the preferred arrangement for the present invention, reference is made to the drawings to enable a more clear understanding of the invention. However, it is to be understood that the inventive features and concept may be manifested in other arrangements and that the scope of the invention is not limited to the embodiments described or illustrated. The scope of the invention is intended only to be limited by the scope of the claims that follow.

The following detailed description of embodiments of the present invention references the accompanying drawings that illustrate specific embodiments in which the invention may be practiced. The embodiments are intended to describe aspects of the technology in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figure 1:
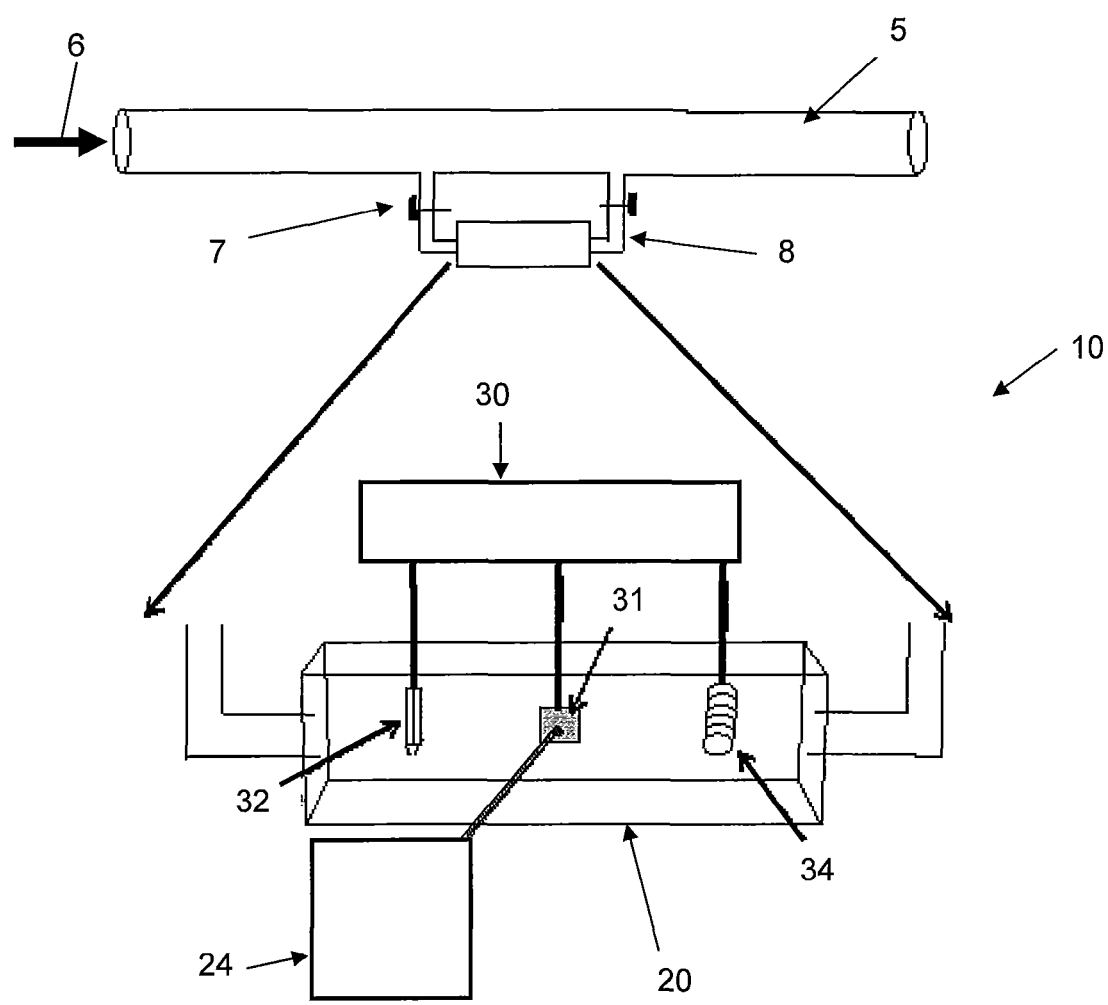
FIG. 1 is a schematic drawing showing a pipeline with an on-line/at-line SERS measurement device for measuring the presence of minute amounts of certain desirable chemicals.

Referring now to FIG. 1, a pipeline 5 is shown carrying liquids in the direction of arrow 6. A sample tap line 7 is arranged to take liquid off the bottom of the pipeline 5 and into a stop flow cell 20. The stop flow cell 20 is a simple chamber or housing where precise measurements of chemical concentrations of residual chemicals may be performed with at least some isolation from the main flow in the pipeline. A return line 8 carries the liquid back into the pipeline 5. Valves may be provided in sample tap line 7 and return line 8 to entirely close the stop flow cell 20, but in some embodiments, it may be acceptable and preferred not to fully isolate the volume of liquids in the stop flow cell 20 from the main flow of the pipeline. In some embodiments, the cell 20 may be a restricted cell where continuous flow is acceptable but where the flow is choked down to reduce turbulence or other causes of variance in measurements. A residual chemical monitoring system generally indicated by the arrow 10 periodically measures the concentration of one or more chemicals in stop flow cell 20. It should be noted that pipeline 5 may carry gaseous fluids where some amounts of liquids may collect at the bottom of the pipe and taking the sample off the bottom tends to provide the best source for monitoring the chemicals of interest for operating a pipeline whether it is an oil line, a gas line or a refined products pipeline.

The residual chemical monitoring system 10 uses spectroscopy analyses and specifically uses Surface Enhanced Raman Spectroscopy or SERS to identify the presence and provide some quantification of the concentrations of certain chemicals in the pipeline 5. The SERS spectroscopy method is described in parent U.S. patent application Ser. Nos. 12/047,141 and 12/116,415 as it relates to laboratory scale testing and laboratory scale application. In this particular application, live liquid is tested in stop flow cell 20 with a flange through which the probe from the light source of an optical component 24 is directed to a test coupon 31. A controller 30 is electrically connected to the coupon 31 and also to reference electrode 32 and a counter electrode 34. The controller 30 controls the potential applied to the coupon 31 for specific measurements of chemicals of interest in the pipe. The controller 30 is preferably automated to adjust the potential applied to the coupon 31 based on the voltage measured by reference electrode 32 and counter electrode 34.

The purpose of the electrical charge on coupon 31 is to attract or draw the target substance or target substances to the surface of the coupon 31. Considering the low percentage at which some of the target substance may be present in the total volume of liquid which would regularly be below 1000 parts per million (ppm) and it would be desirable to identify and quantify target substances down to between 250 to 50 ppm and more preferable to quantify target substance down near 100 ppm. With these low concentrations, attracting the target substances to the surface of the coupon 31 provides the system 10 with an opportunity to recognize the presence and provide an indication of the quantity or the concentration of the target substance or target substances. Indeed, part of the process for reporting the concentration would be to correlate or calibrate by various other quantification methods the relationship of how much of the target substance is measured on the surface as compared to the amount of the target substance in the overall liquid material.

The attraction of the target substances is best performed with a fairly precise voltage or electrical potential applied to the coupon 31 that may be adjusted or optimized. The actual electrical potential applied is influenced by on varying factors such as pH of the sample, temperature of the sample and other factors and the inputted electrical charge on the coupon 31 may be adjusted to obtain the precise surface potential to draw the target substance to the surface. The voltage adjustment will be explained below.

The coupon 31 may be a specimen of any material that is the target of the analysis or test and may be, for example, a piece of metal of the kind used in the pipeline 5 or storage tank if the residual chemical monitoring system is deployed to provide monitoring for a storage tank. Other suitable materials may also be used that are sufficiently active for chemical monitoring, cost effective and would have an acceptable service life in the field. Suitable materials may include gold, silver and copper. The coupon 31 is preferably planar and may present substantially any shape. The coupon 31 also includes some features that enhance the attractiveness of the target substance or target substances to the surface. The coupon 31 is preferably an electrically conductive, but non-corrosive or corrosion resistant material. In the preferred embodiment, a nickel-copper alloy is used that is commonly called Monel. The surface of the nickel-copper alloy is polished and cleaned and provided with a precious metal layer such as gold, silver or copper. Gold is preferred and is applied by an electrochemical or colloidal deposition process. An embodiment of the present invention would include an even distribution of gold particles across the surface of the coupon 31. Optimal performance has been achieved with gold particle sizes in the range of 30-80 nanometers spaced at least 30 to 50 microns apart on the surface. With a nickel-copper alloy coupon having gold thereon creates a coupon 31 that is suited for use in the field where an attracting voltage is provided on the surface to draw the target chemical or target substance to the surface for measurements and later provide a reverse polarity charge on the surface to clear any target chemicals that may have attached to the surface. Thus, future measurements would provide meaningful data on new samples without manually cleaning the coupon as might happen in the lab.

Portions of the coupon 31 may be substantially entirely coated with an electrically and chemically insulating material such that only one face of the coupon is exposed to, and in contact with, the sample liquid. Exposing only one face of the coupon to the sample liquid facilitates determining with precision the total amount of surface area of the coupon 31 that is exposed to the sample liquid, which may be helpful or required in electrochemical preparations of the coupon and consistency in the voltage applied to the coupon during measurements.

The reference electrode 32 connects the controller 30 to a reference fluid that is, in itself, in electrochemical communication with the liquid sample in the cell 20 through a salt bridge. The conductive element of reference electrode 32 does not contact the salt bridge. The reference fluid provides a known electrochemical potential and is used as a base or background potential when, for example, applying an electric potential to the liquid sample within the cell 20. The reference fluid may be a salt solution that includes, for example, silver chloride, potassium chloride, or silver nitrate. The salt bridge provides a physical barrier between the reference fluid and the liquid sample from the pipeline 5 allowing electron migration between the reference fluid and the liquid sample. The salt bridge may include the same salt that is used in the reference fluid. The reference fluid and the salt bridge may further be conventional in nature. The conductive element within electrode 32 may be silver or platinum wire or foil. A sensor in the controller 30, such as a potentiostat, provides a reference voltage for analysis of residual chemical in the liquid sample.

Counter electrode 34 includes a wire encapsulated in electrically insulating material extending from controller 30 to the liquid sample in the cell 20. The voltage applied to the coupon is measured across the coupon 31, the liquid in the cell 20 to the counter electrode 34 while also being measured across the coupon 31, the liquid in the cell 20 and the reference liquid that is physically isolated but in electrochemical communication with the liquid in the cell to reference electrode 32. Controller 30 modulates the voltage applied to the coupon 31 based on feedback through counter electrode 34 using feedback from reference electrode 32 to fine tune the potential applied. Considering that the potential applied to the coupon 31 may alter the electrochemical properties of the sample liquid, the reference electrode provides a more precise indication of the charge actually being applied to the coupon 31 to draw the target chemical or target substance to the surface of the coupon 31. Thus, adjustments are made by the controller 30 to fine tune the electrical potential on the coupon 31 to optimize the attraction of the target substance to the coupon 31.

Once the target material is drawn to the surface of the coupon 31 the surface is illuminated by a light source from optical component 24. The light is preferably a monochromatic light source, such as a laser, where an optical sensor within the optical component 24 is positioned relative to the surface of the coupon 31 so that light emitted from the light source strikes the coupon 31 and is reflected back toward the optical sensor of the optical component 24 according to principles of spectroscopy.

Basically, the monochromatic light excites the molecules on the surface of the coupon 31 and the molecules begin to vibrate. The shape and structure of the molecules are revealed by how they vibrate considering the mass of various elements and the bond structures within the molecules and the locations of the bonds within the molecules. As such, the light is scattered in ways that are often distinctive. The more of the target substance that is present on the surface of the coupon 31, the more monochromatic light is scattered in the characteristic manner.

The light collected by the optical sensor of the optical component 24 is converted to a signal. The analysis of the signal can be interpreted by a spectrometer within controller 30 to indicate the presence and at least some quantitative aspect of the concentration of the target material in the sample. The resulting data can be provided to operators of the pipeline or storage vessel or may be automated to control inputs for chemical dosing stations to provide additional chemicals to provide efficient, but effective protection of the pipeline 5 from corrosion and other operating hazards as discussed above.

Referring back to the fine tuning of the desired electrical potential to be applied to the coupon 31, additional tuning may be accomplished using feedback from the spectrometer based on measured scatter patterns to the extent that slight adjustments to the voltage provides improved sensitivity to the target substance by system 10.

In another embodiment, the liquid sample in the chamber of the cell may be heated by a heating element (not shown) to enhance the action of the target material being drawn to the coupon 31.

It should be noted that while a multifunction probe is preferred for directing light to the coupon 31 from a fixed distance to the surface of the coupon 31 and collecting the scattering of light from the molecules on the surface of the coupon 31, these functions may be accomplished using multiple probes or by a device outside the cell 20 that emits light on coupon 31, and receives the scattered light from molecules on the surface of coupon 31 through a window formed in the wall of the stop cell 20. The window should be formed of a robust, transparent material that allows light to pass through with minimal scattering, and thus is transparent or substantially transparent material such as glass or sapphire. The window may be square or circular and may have a diameter within the range of from about 0.5 cm to about 1.5 cm.

The present technology can be used to generate SERS spectra using relatively low-power optics. For example, the light source 24 may be a laser emitter operable to generate laser light at a power of between 30 mW and 80 mW. The system 10 may be installed remotely on a pipeline and arranged to convey data by wire or wireless communication to one or more locations. For example, the data may be provided to operators from several locations along a pipeline while also providing inputs to automated dosing systems for providing biocides, corrosion inhibitors, scale inhibitors, anti-foaming agents, emulsion breakers, hydrate inhibitors and other preventive or remedial chemical additives.

Figure 2:
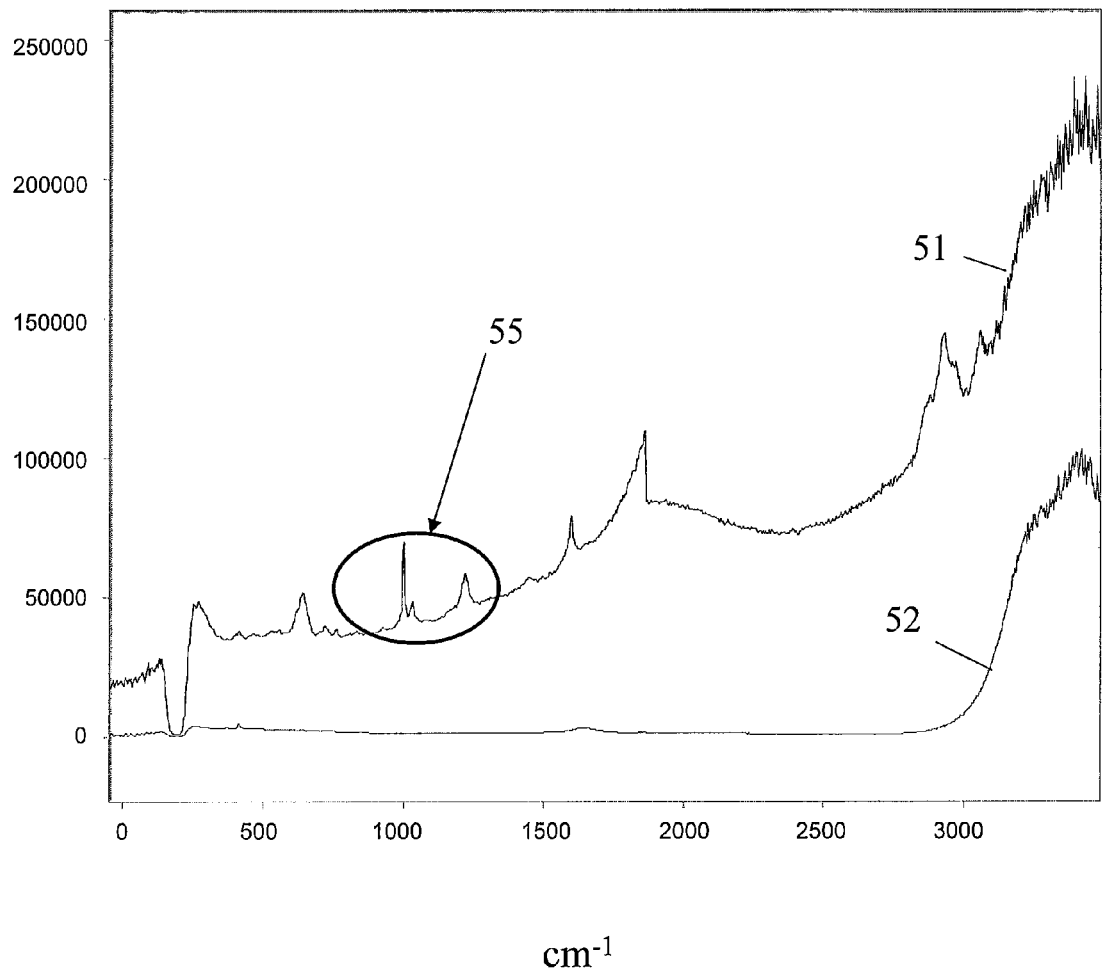
FIG. 2 is a graph showing the effectiveness of the SERS based residual chemical monitoring system of the present invention.

The residual chemical monitoring system was tested using a sample pipeline material that is typically measured. Referring to FIG. 2, measurements of the residual chemical of 300 ppm in brine were performed. The system monitored in normal Raman mode shown by the lower graph 52 and in SERS mode at 51. The normal Raman spectrum 52 contains signals only for water around 1600 and 3300 $cm^{-1}$. By normal Raman, 300 ppm of the inhibitor was not detected and such technology would not provide any feedback that the 300 ppm dosage was present. Although 300 ppm is effective as an inhibitor, a higher amount would have to be injected into the pipeline if Raman spectroscopy were the only available technology for monitoring the sufficient presence of such additives. However, the considerably increased sensitivity of the SERS technology used in the present invention allows the detection and quantification of target substances like additives as shown by graph 51 in FIG. 2. Some of the peaks due to the 300 ppm target material are highlighted by the oval 55. These peaks indicate the presence of the target substance and the height of these peaks indicate its quantity. Higher peaks mean higher concentration, however, some calibration and correlation of the height of the peaks is necessary to provide meaningful concentrations. The higher ability to detect target chemicals that are additives would allow a lower dosing of the inhibitor or other additives that would reduce cost while maintaining effectiveness.

Although the invention has been described with reference to the embodiments illustrated in the attached drawing figures, it is noted that equivalents may be employed and substitutions made herein without departing from the scope of the invention as recited in the claims. For example, the particular form or function of the various attachment elements is not important to the present technology, and the attachment elements may present alternative shapes and sizes with equally-preferred results.

As used herein, a "conductor," "conductive element," or conductive material" is a material with an electrical resistivity of less than about $1 \times 10^{-3}$ Ωm and more preferably less than about $1 \times 10^{-5}$ Ωm.

As used herein, an "insulator," "insulating element," or "insulating material" is a material with an electrical resistivity of more than about 100 Ωm and more preferably more than about $1 \times 10^3$ Ωm.

Finally, the scope of protection for this invention is not limited by the description set out above, but is only limited by the claims which follow. That scope of the invention is intended to include all equivalents of the subject matter of the claims. Each and every claim is incorporated into the specification as an embodiment of the present invention. Thus, the claims are part of the description and are a further description and are in addition to the preferred embodiments of the present invention. The discussion of any reference is not an admission that it is prior art to the present invention, especially any reference that may have a publication date after the priority date of this application.

The invention claimed is:

1. A system for determining the presence and concentration of a target substance within a liquid material in a pipeline or vessel, said device comprising:
- a chamber connected in fluid communication to the pipeline or vessel and arranged to receive and accumulate samples of a liquid material directly from the pipeline or vessel through an inlet and return samples back to the pipeline or vessel;
- a coupon within the chamber having an electrically conductive surface;
- an electrical charging system for providing an electric charge on the coupon;
- a counter electrode within the vessel and spaced from the coupon for sensing an electric charge on the coupon and through a sample liquid material within the vessel;
- a reference electrode within the chamber and spaced from each of the coupon and the counter electrode and arranged for sensing an electric charge on the electrode and through a sample liquid material within the chamber and also through a reference fluid that is physically isolated from any sample liquid material in the vessel but in electrochemical communication with any sample liquid within the vessel;
- an electrical charging system arranged to provide the electric charge on the coupon and adjusting the precise electrical charge based on input from the counter electrode and reference electrode so as to provide a precise electric charge that draws molecules of the target substance to the surface of the coupon;
- an optical component with a light source for directing light to the electrically conductive surface of the coupon to induce vibrational responses of and within the molecules of the liquid material and a sensor for collecting and measuring light scattered by the vibrating molecules on the surface of the coupon;
- a spectrometer for interpreting the scattered light to provide information regarding the presence and quantificational information of the target substance within the liquid material in the pipeline or vessel.

2. The system according to claim 1 wherein the coupon is a nickel-copper alloy.

3. The system according to claim 2 wherein the surface of the coupon includes a precious metal coating.

4. The system according to claim 3 wherein the precious metal comprises gold, silver and copper.

5. The system according to claim 4 wherein the precious metal is gold.

6. The system according to claim 3 wherein the precious metal is an electrochemical deposition.

7. The system according to claim 3 wherein the precious metal is a colloidal deposition.

8. The system according to claim 4 wherein the inlet into the chamber includes a valve arranged to open and close such that when it is open, it allows liquid flow into the chamber and when closed, it prevents flow into the chamber.

9. The system according to claim 8 further including a valve in the return line to further isolate the chamber from the pipeline or vessel.

10. The system according to claim 1 further including a radio communication device for remote communication of the presence and concentration information of the target substance to other locations.

11. The system according to claim 1 further including a wireline communication device for remote communication of the presence and concentration information of the target substance to other locations.

12. The system according to claim 1 wherein the spectrometer includes a detection device for converting the scattered light into a signal that represents at least one characteristic aspect of the chemical structure of the molecules on the surface of the coupon and further includes an interpreter for converting the signal into an indication of the present and concentration of the target substance.

13. The system according to claim 1 wherein the light source of the optical component is a laser.

* * * * *